(12) United States Patent
Williams

(10) Patent No.: US 6,350,926 B1
(45) Date of Patent: *Feb. 26, 2002

(54) CHLOROFLUOROHYDROCARBON AND PROCESS THERETO

(75) Inventor: Alfred Glyn Williams, Binfield (GB)

(73) Assignee: Syngenta Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/460,912

(22) Filed: Dec. 14, 1999

Related U.S. Application Data

(63) Continuation of application No. 09/005,166, filed as application No. PCT/GB97/00653 on Mar. 11, 1997, now Pat. No. 6,075,172, which is a continuation-in-part of application No. 08/706,948, filed on Sep. 3, 1996.

(30) Foreign Application Priority Data

Feb. 27, 1997 (GB) .............................. 9704057

(51) Int. Cl.[7] .......................... C07C 17/08; C07C 19/08

(52) U.S. Cl. ...................... 570/169; 570/134; 570/166; 570/167; 570/168

(58) Field of Search ................................ 570/134, 169, 570/166, 167, 168

(56) References Cited

U.S. PATENT DOCUMENTS 5,032,648 A 7/1991 Nicholas
5,852,222 A * 12/1998 Williams et al. ............ 570/134

FOREIGN PATENT DOCUMENTS

DE 1156771 11/1963
EP 699649 3/1996

* cited by examiner

*Primary Examiner*—Alan Siegel
(74) *Attorney, Agent, or Firm*—Hale and Dorr LLP

(57) ABSTRACT

The present invention provides the novel chlorofluorohydrocarbon 1,1-difluoro-1,4-dichlorobutane, and a process for its preparation comprising reacting 1,1,1,4-tetrachlorobutane or 1,1,4-trichlorobut-1-ene with hydrogen fluoride in the liquid or vapour phase. The product has useful solvent properties and is also useful in synthetic chemistry for the introduction of fluorocarbon functionality.

19 Claims, No Drawings

CHLOROFLUOROHYDROCARBON AND PROCESS THERETO

This is a continuation of application Ser. No. 09/005,166 filed on Jan. 9, 1998 now U.S. Pat. No. 6,025,172 which is a 371 national phase of PCT/GB97/00653 filed Mar. 11, 1997 which is a continuation-in-part of application Ser. No. 08/706,948 filed on Sep. 3, 1996.

The present invention relates a novel chlorofluorohydrocarbon and to a novel process for its preparation. More particularly it relates to 1,1-difluoro-1,4-dichlorobutane and processes for preparing it from the known compounds 1,1,1,4-tetrachlorobutane and 1,1,4-trichlorobut-1-ene.

Accordingly the present invention provides 1,1-difluoro-1,4-dichlorobutane.

In a further aspect the present invention provides a process for preparing 1,1-difluoro-1,4-dichlorobutane comprising reacting 1,1,1,4-tetrachlorobutane or 1,1,4-trichlorobut-1-ene with hydrogen fluoride in the liquid or vapour phase.

The process of the present invention is illustrated using 1,1,1,4-tetrafluorobutane as starting material by the following reaction scheme:

The reaction is conveniently conducted in a vessel whose lining is resistant to corrosion by chemical reaction with hydrogen fluoride, such as for example, one made from "Hastalloy" (Registered Trade Mark) or Monel metal. When the reaction is conducted in the vapour phase it is conveniently conducted by passing a stream comprising a mixture of the reactants through a heated reaction zone, preferably defined by a tubular vessel.

The reaction can conveniently be carried out in the presence of a catalyst such as a polyvalent metal halide or aluminium oxide.

Examples of suitable catalysts for liquid phase reactions include titanium halides, ferric chloride, particularly in the presence of activated charcoal, aluminium fluoride, aluminium oxide (γ-alumina), chromium fluoride, manganese difluoride, ferric fluoride, cobalt dichloride, nickel difluoride, zirconium fluoride, thorium fluoride, boron trifluoride, tantalum trifluoride, oxyfluorides and antimony pentachloride, particularly in the presence of activated charcoal.

Titanium halides which are suitable for use in liquid phase reactions include titanium chlorides, titanium fluorides and titanium bromides, particularly titanium (VI) chloride.

Tin halides are preferred catalysts for liquid phase reactions and a particularly useful catalyst is tin (IV) chloride.

Examples of suitable catalysts for vapour phase reactions include halides of aluminium, iron, chromium, vanadium, tungsten, tantalum, antimony, titanium, tin, zirconium, nickel, niobium, molybdenum, manganese, cobalt, thorium and mercury. Examples of specific catalysts include ferric chloride, particularly in the presence of activated charcoal, aluminium fluoride, aluminium oxide (λ-alumina), chromium halides such as chromium chloride and chromium fluoride, manganese difluoride, ferric fluoride, cobalt dichloride, nickel difluoride, zirconium fluoride, thorium fluoride, oxyfluorides and antimony pentachloride, particularly in the presence of activated charcoal.

Chromium halides are preferred catalysts for vapour phase reactions and a particularly useful catalyst is chromium (III) chloride. The catalyst may be supported on alumina, which has preferably been pre-treated with a fluorinating agent such as sulfur tetrafluoride, so as to convert it, at least in part, to aluminium trifluoride.

For liquid phase reactions the reaction temperature is preferably in the range 50 to 150° C., and more preferably in the range 70 to 90° C. The duration of the reaction is usually in the range 4 to 10 hours.

For vapour phase reactions the reaction temperature is preferably in the range 100 to 400° C., and more preferably in the range 135 to 250° C. The reaction may be conducted under atmospheric pressure or at a pressure above atmospheric pressure, provided that the combination of pressure and temperature is chosen so as to ensure that the reactants and products remain in the vapour phase. The conversion rate is also dependent on various factors such as the residence time in the reaction zone, the ratios of the reactants and the concentration of the reactants as well as the presence of other components of the vapour stream. Preferably the stream contains an inert gaseous diluent to moderate the reaction, nitrogen is suitable for this purpose. The reactants and other components of the vapour stream should be free of any water.

The reaction is carried out using hydrogen fluoride which is a volatile material having a boiling point under normal atmospheric pressure of 19.5° C; In order to conduct the reaction in the liquid phase a sealed reaction vessel may be used in which the reaction proceeds under the autogenic pressure of the reactants and products. In a preferred variant of the liquid phase process a vessel can be used which is equipped with means to permit the hydrogen chloride produced during the reaction to be vented, preferably continuously, whilst the reaction is maintained in the liquid phase by the autogenic pressure of the reactants and products. This may be achieved by the use of a condenser which liquefies evaporating hydrogen fluoride whilst permitting the escape of the more volatile hydrogen chloride gas. Such an arrangement permits the autogenic pressure to be maintained in the range of about 175 to about 500 psi, e.g. about 175 to about 230 psi.

The vapour phase reaction is preferably carried out by passing a gaseous mixture of hydrogen fluoride together with 1,1,1,4-tetrachlorobutane or 1,1,4-trichlorobut-1-ene at an elevated temperature diluted with nitrogen through a reaction zone defined by a metal tube heated to a temperature in the range 130 to 250° C., and thereafter cooling the reactant stream so as to condense out the mixture of reactants and products, which can then be separated by fractional distillation. In a preferred variant of the vapour phase process a receiving vessel can be used which is equipped with means to permit the hydrogen chloride produced during the reaction to be vented, preferably continuously. This may be achieved by the use of a condenser which liquefies the hydrogen fluoride and the other less volatile components whilst permitting the escape of the more volatile hydrogen chloride gas.

The product mixture consists principally of the desired 1,1-difluoro-1,4-dichlorobutane, with minor quantities of other materials present including unreacted starting material and intermediate species formed during the process, for example 1,1,1-trifluoro-4-chlorobutane. When the reaction is conducted in the liquid phase at a temperature of 85 to 90° C. with venting of the hydrogen chloride over a 6 to 7 hour period good yields and conversion rates may be obtained with minimal co-production of 1,1,1-trifluoro-4-chlorobutane. Isolation of the desired product can readily be achieved by fractional distillation and the unreacted starting material and intermediate species recycled back into the reactant stream. One such intermediate species formed during the process when 1,1,1,4-tetrachlorobutane is used as starting material is 1,1,4-trichlorobut-1-ene.

1,1-Difluoro-1,4-dichlorobutane is a novel compound which has useful properties as a solvent, and may be used, for example, in degreasing electrical and electronic components such as printed circuits and the like. Because of its higher boiling point and lower volatility compared with the halomethanes and haloethanes traditionally used for degreasing, and the fact that it is a chlorofluorohydrocarbon and not a chlorofluorocarbon, its use may have environmental advantages. It is also of use as a synthetic chemical intermediate particularly for introducing fluorocarbon functionality into a molecule, for example as a means of introducing the difluorobutenyl group into the nematicidal compounds of International Patent Applications WO 94/06777 and WO 95/24403.

Various further preferred features and embodiments of the present invention will now be described with reference to the following non-limiting examples, in which Examples 1 to 7 relate to liquid phase reactions and Examples 8 to 10 relate to vapour phase reactions. It will be understood that whereas the Examples disclose experimental procedures which show that the process of the invention can be used to produce the desired product, they may not necessarily disclose the most advantageous conditions for ensuring the economically optimal production of the desired product. Such conditions would be established by a process of routine examination of variation of the conditions within the alternatives and ranges set out herein and any such optimised process may be considered as being included within the scope of the invention.

The following abbreviations are used in the Examples:

NMR-nuclear magnetic resonance;

t-triplet;

m-multiplet;

br-broad;

MS-mass spectrum;

GC-gas chromatography.

Chemical shifts (δ) are measured in parts per million from tetramethylsilane. $CDCl_3$ was used as solvent for NMR spectra unless otherwise stated.

EXAMPLE 1

Preparation of 1,1-difluoro-1,4-dichlorobutane from 1,1,1,4-tetrachlorobutane 1,1,1,4-Tetrachlorobutane (5 g, 25 mmol) was charged to a 25 ml Monel autoclave, which was then purged. Hydrogen fluoride (10.6 g, 535 mmol) was added as a liquefied gas, the stirrer started and the vessel heated to 80° C. at a ramp rate of 1° C./min where it was stirred for 18 hours by which time the pressure had increased to 298 psi. The heating was turned off to allow the reaction to cool to room temperature. After the temperature had dropped to ca. 20° C. the vessel was cooled in an ice/IMS bath and the excess pressure (154 psi at room temperature) vented via a stirred water trap keeping the internal temperature <0° C. to reduce the loss of entrained volatile products. On completion of the venting the vessel was opened and the dark red reaction mixture was poured carefully onto ice (ca. 50 g), the organic phase separated, small amounts of sodium fluoride and magnesium sulfate were added to absorb any hydrogen fluoride and water. The weight of the liquid before the addition of the $NaF/MgSO_4$ was 1.7 g. The aqueous liquors were extracted with dichlorobenzene (2×30 ml) and the extracts backwashed with water and dried ($MgSO_4$).

Analysis by GC of the recovered 1.7 g of sample indicated: 0% starting material, 11% 1-fluoro-1,1,4-trichlorobutane, 57% 1,1-difluoro-1,4-dichlorobutane (desired product).

$^1$H NMR: 2.15 (m, 2H, $CH_2$); 2.50 (m, 2H, $CH_2CF_2Cl$); 3.55 (br t, 2H, $CH_2Cl$).

MS: 142 ($M^+$-HF), 127 ($M^+$-Cl).

EXAMPLE 2

Preparation of 1,1-difluoro-1,4-dichlorobutane from 1,1,1,4-tetrachlorobutane 1,1,1,4-Tetrachlorobutane (5.5 g, 28 mmol) was charged to a 25 ml Monel autoclave, which was then purged. Hydrogen fluoride (10.1 g, 505 mmol) was added as a liquefied gas the stirrer started and the vessel heated to 30° C. at a ramp rate of 1° C./min. The initial pressure at this temperature was 27 psi, this rose to 36 psi while the reaction was stirred overnight. This rate of pressure increase was not considered to be sufficient so the reaction temperature was increased to 50° C. and the reaction stirred for a further 23 hours while the pressure increased from 47 psi to 106 psi. The vessel was cooled in an ice/IMS bath and the excess pressure (72 psi at room temperature) vented via a stirred water trap keeping the internal temperature <0° C. to reduce the loss of entrained volatile products. On completion of the venting the vessel was opened and the dark red reaction mixture was poured carefully onto ice (ca. 50 g) and the organic phase separated, small amounts of sodium fluoride and magnesium sulfate were added to the straw coloured liquid to absorb any hydrogen fluoride and water. The damp weight of the material was 2.85 g. The aqueous liquors were extracted with dichlorobenzene (2×30 ml) and the extracts backwashed with water and dried ($MgSO_4$).

GC analysis indicated the presence of 1,1-difluoro-1,4-dichlorobutane.

EXAMPLE 3

Preparation of 1,1-difluoro-1,4-dichlorobutane from 1,1,1,4-tetrachlorobutane 1,1,1,4-Tetrachlorobutane (4.9 g, 25 mmol) was charged to a 25 ml Monel autoclave, which was then purged. Hydrogen fluoride (10.7 g, 535 mmol) was added as a liquefied gas, the stirrer started and the vessel heated to 65° C. at a ramp rate of 1° C./min. The initial pressure at this temperature was ca. 70 psi, this rose to 184 psi over the next 23 hours. After allowing the temperature to drop to ca. 20° C. the vessel was cooled in an ice/IMS bath and the excess pressure (120 psi at room temperature) vented via a stirred water trap (no indication of carry over into this trap) keeping the internal temperature <0° C. to reduce the loss of entrained volatile products (the weight of the vessel dropped by approx. 1 g during this process). On completion of the venting the vessel was opened and the dark red reaction mixture was poured carefully onto ice (ca. 50 g) and the organic phase separated, small amounts of sodium fluoride and magnesium sulfate were added to the straw coloured liquid to absorb any hydrogen fluoride and water. Dam p weight of material was ca. 1 g. The aqueous liquors were extracted with dichlorobenzene (2×30 ml) and the extracts backwashed with water and dried ($MgSO_4$).

GC analysis indicated the presence of the desired product, 1,1-difluoro-1,4-dichlorobutane.

EXAMPLE 4

Preparation of 1,1-difluoro-1,4-dichlorobutane from 1,1,1,4-tetrachlorobutane 1,1,1,4-Tetrachlorobutane (2.0 g, 10 mmol) was charged to a 25 ml Monel autoclave, which was then purged. Hydrogen fluoride (9.8 g, 490 mmol) was added as a liquefied gas, the stirrer started and the vessel heated to 80° C. at a ramp rate of 1° C./min. The initial pressure at this temperature was 113 psi, this rose to 161 psi over the next 2 hours 20 min before the reaction was left to stir overnight at 80° C. The heating was discontinued and reaction allowed to cool to room temperature. The vessel was cooled in an ice/IMS bath and the excess pressure (78 psi at room temperature) vented via a caustic scrubber keeping the internal temperature <0° C. to reduce the loss of entrained volatile products. On completion of the venting the vessel was opened and the dark red reaction mixture was poured carefully onto ice (ca. 50 g) and the organic phase extracted into dichloromethane (3×15 ml). The extracts were analysed by GC which suggested that there were two major products (>5% level) with no starting material left. The extracts were dried (MgSO$_4$) and the dichloromethane distilled off at atmospheric pressure to give 1.76 g of a dark liquid.

GC analysis indicated that the recovered sample contained 36% of the desired product, 1,1-difluoro-1,4-dichlorobutane.

EXAMPLE 5

Preparation of 1,1-difluoro-1,4-dichlorobutane from 1,1,1,4-tetrachlorobutane in the presence of tin (IV) chloride 1,1,1,4-Tetrachlorobutane (35.3 g), liquefied hydrogen fluoride (20.5 g) and tin (IV) chloride (2.6 ml) were charged sequentially at −20° C. into a Monel autoclave fitted with a metal condenser cooled to −15° C. and topped with a needle valve to permit venting of gases. The autoclave temperature was raised to 90° C. at ramp rate of 2° C./min and maintained at this temperature for 4 hours with periodic venting of the hydrogen chloride produced so as to maintain the internal pressure within the range 180 to 220 psi. The autoclave was then cooled to −10° C. and the contents added carefully to ice (50 g). After allowing the ice to melt the mixture was extracted with dichloromethane (2×20 ml), the extracts combined and dried over sodium fluoride and magnesium sulfate, and the product mixture recovered by evaporation of solvent.

GC analysis indicated the presence of a mixture of ca. 79% of the desired 1,1-difluoro-1,4-dichlorobutane and 18% of 1,1,1-trifluoro-4-chlorobutane.

The 1,1-difluoro-1,4-dichlorobutane was separated by fractional distillation and obtained as a colourless liquid (20.74 g, bp 63–65° C. at 138 mbar).

EXAMPLE 6

Preparation of 1,1-difluoro-1,4-dichlorobutane from 1,1,1,4-tetrachlorobutane in the presence of titanium (IV) chloride 1,1,1,4-Tetrachlorobutane (35.3 g), liquefied hydrogen fluoride (20.5 g) and titanium (IV) chloride (2.6 ml) were charged sequentially at −20° C. into a Monel autoclave fitted with a metal condenser cooled to −15° C. and topped with a needle valve to permit venting of gases. The autoclave temperature was raised to 90° C. at ramp rate of 2° C./min and maintained at this temperature for 4 hours with periodic venting of the hydrogen chloride produced so as to maintain the internal pressure within the range 180 to 220 psi. The autoclave was then cooled to −10° C. and the contents added carefully to ice (50 g). After allowing the ice to melt the mixture was extracted with dichloromethane (2×20 ml), the extracts combined and dried over sodium fluoride and magnesium sulfate, and the product mixture recovered by evaporation of solvent. The 1,1-difluoro-1,4-dichlorobutane was separated by fractional distillation and obtained as a colourless liquid.

EXAMPLE 7

Preparation of 1,1-difluoro-1,4-dichlorobutane from 1,1,4-trichlorobut-1-ene

A 300 ml Parr reactor, fitted with a condenser cooled to −10° C. and topped with a needle valve to permit venting of gases, was purged with nitrogen and 1,1,4-trichlorobut-1-ene (45.4 g, 271 mmol) was charged to the reactor. The reactor was cooled to −35° C. and hydrogen fluoride (27.2 g, 1360 mmol) was added as a liquefied gas, the reaction was heated to 90° C. with stirring for a total of 12 hours maintaining the pressure at about 110 psi. The reaction was allowed to cool to room temperature then cooled to −20° C. in a dry ice/acetone bath. The reaction mixture was discharged into a stirred solution of KOH in ice/water, the pH adjusted to 14 by the addition of further KOH solution and the organic phase separated.

Analysis by GC of the crude sample indicated the presence of the desired 1,1-difluoro-1,4-dichlorobutane, unreacted starting material and 1-fluoro-1,1,4-trichlorobutane.

EXAMPLE 8

Preparation of a Chromium (III) Chloride Catalyst Supported on Aluminium Fluoride Alumina pellets (150 g) were packed into a Hastalloy hot tube reactor (length 420 mm, internal diameter 25 mm) and dried by heating for 30 min to 240° C. whilst nitrogen gas was passed through the bed at a rate of 1.0 l/min. The reactor tube was then cooled to 26° C. and sulfur tetrafluoride passed into the tube. The internal temperature increased steadily over 17 min to 160° C. then slowly decreased to 70° C. after which the flow of sulfur tetrafluoride was stopped. After restarting the flow of sulfur tetrafluoride the temperature was observed to increase slowly to 75° then over 6 min further increased very rapidly to 265° C. after which the flow was stopped and the tube cooled to 75° C. The flow of sulfur tetrafluoride was recommenced and a slow exotherm to 90° C. over 10 min observed after which the tube was cooled to 57° C. and the nitrogen purge continued for 1.0 hour. The flow of sulfur tetrafluoride was restarted and continued for a further 15 min and then stopped. The total amount of sulfur tetrafluoride used was 380 g.

Chromium III chloride (45 g) was suspended in methanol (450 ml) and warmed to 35° C. Zinc powder (1.0 g) was added and the mixture stirred for 35 min, a further 0.35 g of zinc added, heated to 40° C. for a further 10 min and then at 50° C. followed by addition of a further 1.0 g of zinc, followed by one drop of concentrated hydrochloric acid. The temperature of the mixture was observed to increase from 45 to 65° C. (controlled with an ice bath) as the chromium (III) chloride dissolved giving a green slightly cloudy solution. The solution was cooled to ambient and filtered through HiFlo to remove a trace of suspended solids. The volume of the solution was reduced by half by rotary evaporation and the resultant concentrated solution was added to the fluoridated pellets prepared as above after they had been dried by heating to 80° C. and cooled to ambient temperature under a nitrogen atmosphere. The slurry of pellets was agitated periodically and the remaining solvent removed by evaporation under reduced pressure. Methanol (50 ml) was added, the pellets slurried and the excess solvent removed on the rotary evaporator. The pellets were heated to 80° C. under vacuum then allowed to cool under nitrogen. Acetonitrile (50 ml) was added to the pellets and the slurry and after 16 hours the pellets were filtered to remove excess liquid and dried by heating to 80° C. under vacuum for 2 hours. At this stage the pellets were grey green in colour.

The pellets were charged to the Hastalloy hot tube reactor, a chloros scrubber was fitted to the reactor exit and the pellets heated to 370° C. for 4½ hours under a stream of nitrogen then cooled to ambient. After 24 hours the packed tube was reheated to 370° C. for 5¾ hours then stood for 17 hours at ambient temperature. The reactor tube was heated to 150° C. and gaseous hydrogen fluoride passed through at a rate of 200 ml/min with nitrogen. A steady exotherm occurred with the temperature increasing to a maximum of 192° C. After 15 min the temperature began to decrease and at 175° C. the flow of hydrogen fluoride was stopped and the catalyst pellets allowed to cool under a nitrogen atmosphere.

The hot tube reactor containing the catalyst was then used in the process described in Example 9.

EXAMPLE 9

Preparation of 1, 1-difluoro-1,4-dichlorobutane from 1,1,1,4-tetrachlorobutane

The Hastalloy hot tube reactor containing the chromium (III) chloride catalyst prepared in Example 8 was fitted at one end with inlet ports to allow controlled ingress of gaseous hydrogen fluoride, and 1,1,1,4-tetrachlorobutane and a flow of nitrogen, and was connected at the other end to a cold trap maintained at −78° C. The tube was heated to 160° C. and the nitrogen flow rate set at 200 ml/min. Hydrogen fluoride (19.4 g) was fed at a rate of 300 ml/min and 1,1,1,4-tetrachlorobutane (2.0 ml) fed at a rate of 0.1 ml/min. The hydrogen fluoride addition was continued for 3 min after the tetrachlorobutane addition was complete. The contents of the cold trap were collected by washing out with dichloromethane (5×10 ml) the washings combined and treated with iced water to remove hydrogen fluoride and the organic phase washed with water and dried ($MgSO_4$). The solvent was removed by careful distillation using a knitmesh column (length 77 mm, diameter 8 mm) and the residual liquid analysed by GC/MS, revealing that the product mixture contained 1,1-difluoro-1,4-dichlorobutane, unreacted 1,1,1,4-tetrachlorobutane and 1,1,4-trichlorobut-1-ene in the ratio 7:32:2.

Data for 1,1-difluoro-1,4-dichlorobutane:

$^1$H NMR: 2.15 (m, 2H, $CH_2$); 2.50 (m, 2H, $CH_2CF_2Cl$); 3.55 (br t, 2H, $CH_2Cl$).

MS: 142 (M+−HF), 127 (M+−Cl).

EXAMPLE 10

Preparation of 1,1-difluoro-1,4-dichlorobutane from 1,1,4-trichlorobut-1-ene

A Hastalloy hot tube reactor containing aluminium trifluoride catalyst was fitted at one end with inlet ports to allow controlled ingress of gaseous hydrogen fluoride, and 1,1,4-trichlorobut-1-ene and a flow of nitrogen, and was connected at the other end to a cold trap maintained at −78° C. The tube was heated to 190° C. and the nitrogen flow rate set at 48 ml/min. Hydrogen fluoride (4.0 g) was fed at a rate of 0.7 g/hour and 1,1,4-trichlorobut-1-ene (16 g) fed at a rate of 2.32 g/hour. The hydrogen fluoride addition was continued for 3 min after the tetrachlorobutane addition was complete. The contents of the cold trap were collected by washing out with dichloromethane (5×10 ml) the washings combined and treated with iced water to remove hydrogen fluoride and the organic phase washed with water and dried ($MgSO_4$). The residual liquid was analysed by GC/MS, revealing that the product mixture contained 1,1-difluoro-1,4-dichlorobutane and unreacted 1,1,4-trichlorobut-1-ene.

What is claimed is:

1. A process for preparing 1,1-difluoro-1,4-dichlorobutane comprising reacting 1,1,1,4-tetrachlorobutane or 1,1,4-trichlorobut-1-ene with hydrogen fluoride in the vapour phase.

2. A process according to claim 1 carried out in the presence of a catalyst selected from polyvalent metal halides and aluminium oxides.

3. A process according to claim 2 wherein the polyvalent metal halide is selected from halides of aluminium, iron, chromium, vanadium, tungsten, antimony, tantalum, titanium, zirconium, tin, nickel, niobium, molybdenum, and mercury.

4. A process according to claim 2 wherein the polyvalent metal halide is selected from ferric chloride, aluminium fluoride, chromium chloride, chromium fluoride, manganese difluoride, ferric fluoride, cobalt dichloride, nickel difluoride, zirconium fluoride, thorium fluoride, oxyfluorides and antimony pentachloride, optionally in the presence of activated charcoal.

5. A process according to claim 3 wherein the polyvalent metal halide is selected from chromium halides.

6. A process according to claim 5 wherein the chromium halide is chromium (III) chloride.

7. A process according to claim 2 carried out at a temperature within the range 100 to 400° C.

8. The process of claim 2, wherein the catalyst is supported on alumina.

9. The process of claim 8, wherein the alumina has been pre-treated with a fluorinating agent.

10. The process of claim 9, wherein the fluorinating agent is sulfur tetrafluoride.

11. The process of claim 7, carried out at a temperature in the range of 135 to 250° C.

12. The process of claim 2, wherein the reaction is conducted at atmospheric pressure.

13. The process of claim 2, wherein the reaction is conducted at a pressure above atmospheric pressure.

14. The process of claim 2, further comprising cooling the reactant stream to condense out the reactants and 1,1-difluoro-1,4-dichlorobutane.

15. The process of claim 14, further comprising separating the reactants and 1,1-difluoro-1,4-dichlorobutane by fractional distillation.

16. The process of claim 2, wherein hydrogen chloride produced by the reaction is vented during the reaction.

17. The process of claim 16, wherein the wherein hydrogen chloride produced by the reaction is continuously vented during the reaction.

18. The process of claim 2, comprising reacting 1,1,1,4-tetrachlorobutane with hydrogen fluoride in the vapour phase.

19. The process of claim 2, comprising reacting 1,1,4-trichlorobut-1-ene with hydrogen fluoride in the vapour phase.

* * * * *